(12) United States Patent
Mosier

(10) Patent No.: US 8,985,101 B2
(45) Date of Patent: Mar. 24, 2015

(54) METHOD AND DEVICE FOR CLAMPING A BLISTER WITHIN A DRY POWDER INHALER

(71) Applicant: Microdose Therapeutx, Inc., Monmouth Junction, NJ (US)

(72) Inventor: Kent D. Mosier, Princeton, NJ (US)

(73) Assignee: Microdose Therapeutx, Inc., Monmouth Junction, NJ (US)

( * ) Notice: Subject to any disclaimer, the term of this patent is extended or adjusted under 35 U.S.C. 154(b) by 0 days.

(21) Appl. No.: 13/840,577

(22) Filed: Mar. 15, 2013

(65) Prior Publication Data

US 2013/0213392 A1    Aug. 22, 2013

Related U.S. Application Data

(63) Continuation-in-part of application No. 12/785,082, filed on May 21, 2010.

(60) Provisional application No. 61/180,396, filed on May 21, 2009.

(51) Int. Cl.
| | | |
|---|---|---|
| *A61M 16/00* | (2006.01) | |
| *A61M 15/00* | (2006.01) | |
| *A61M 11/00* | (2006.01) | |

(52) U.S. Cl.
CPC ......... *A61M 15/0091* (2013.01); *A61M 11/005* (2013.01); *A61M 15/0045* (2013.01); *A61M 15/0085* (2013.01); *A61M 2016/0024* (2013.01); *A61M 2016/0033* (2013.01);
(Continued)

(58) Field of Classification Search
USPC ............. 128/203.12, 203.15, 203.19, 203.21, 128/200.11–200.23, 3.15; 604/58, 604/93.01–95.01, 403; 222/144, 168.5, 222/167–168
See application file for complete search history.

(56) References Cited

U.S. PATENT DOCUMENTS

| 2,517,482 | A | 8/1950 | Hall |
| 3,507,277 | A | 4/1970 | Altounyan et al. |
| (Continued) | | | |

FOREIGN PATENT DOCUMENTS

| DE | 102005005540 | 8/2006 | ............ A61M 15/00 |
| DE | 102009005048 | 7/2010 | ............ A61H 31/02 |
| (Continued) | | | |

OTHER PUBLICATIONS

Chinese Office Action issued in corresponding Chinese Patent Application Serial No. 201080022180.3, dated Jan. 14, 2013, with translation. (12 pgs).

(Continued)

*Primary Examiner* — Melanie Hand
*Assistant Examiner* — Ned T Heffner
(74) *Attorney, Agent, or Firm* — Hayes Soloway P.C.

(57) ABSTRACT

The present disclosure provides an inhaler having a vibration element for aerosolizing medicament contained in a blister pack, wherein individual blister packs are positioned within the housing to be simultaneously engaged with the flow channel and the vibration element. The flow channel includes a blister pack clamping surface that engages the blister pack near the top of the crown and allows the blister three rotational degrees of freedom. The advantages of this arrangement include improved consistency and higher airspeed of the synthetic jet, as well as other advantages.

**11

Figure 1A:
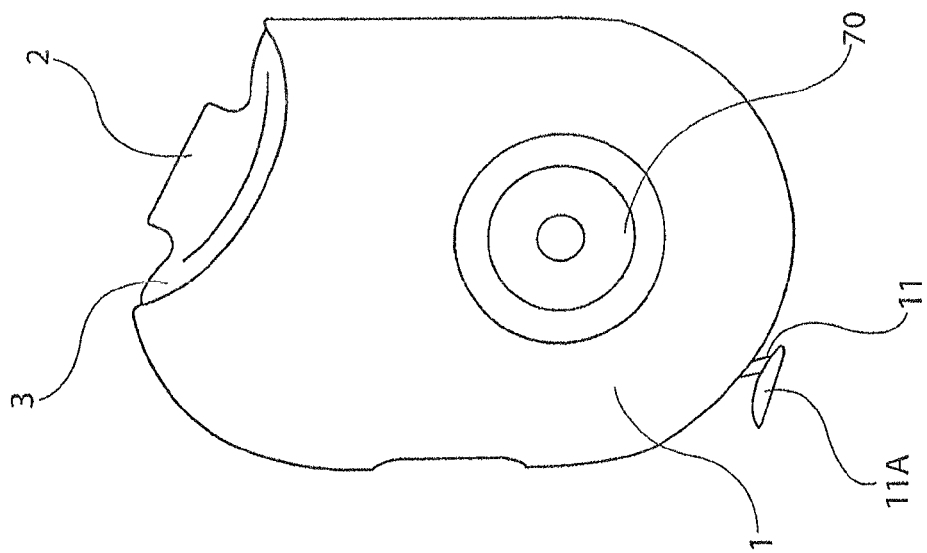
Figure 1B:
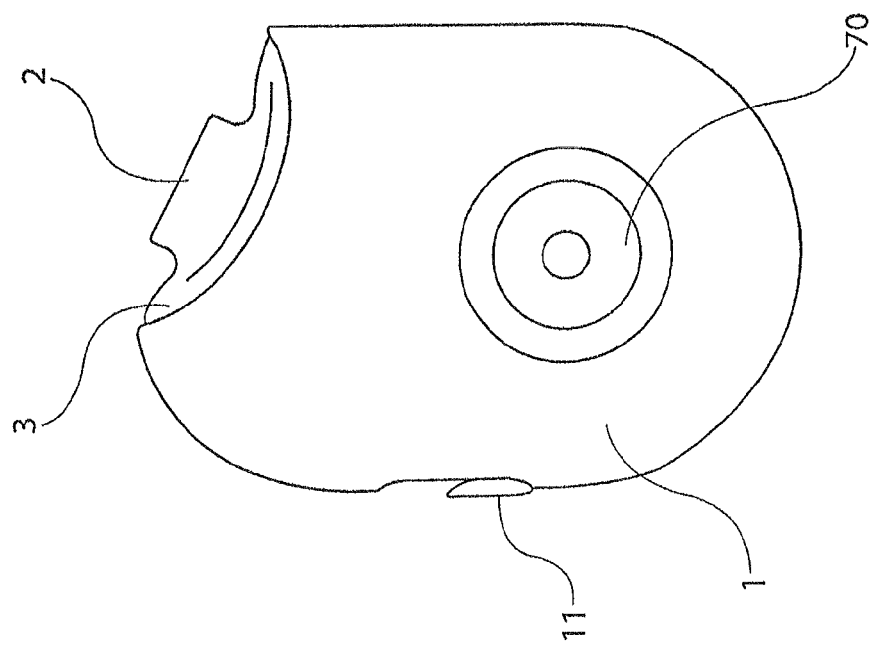
Figure 2A:
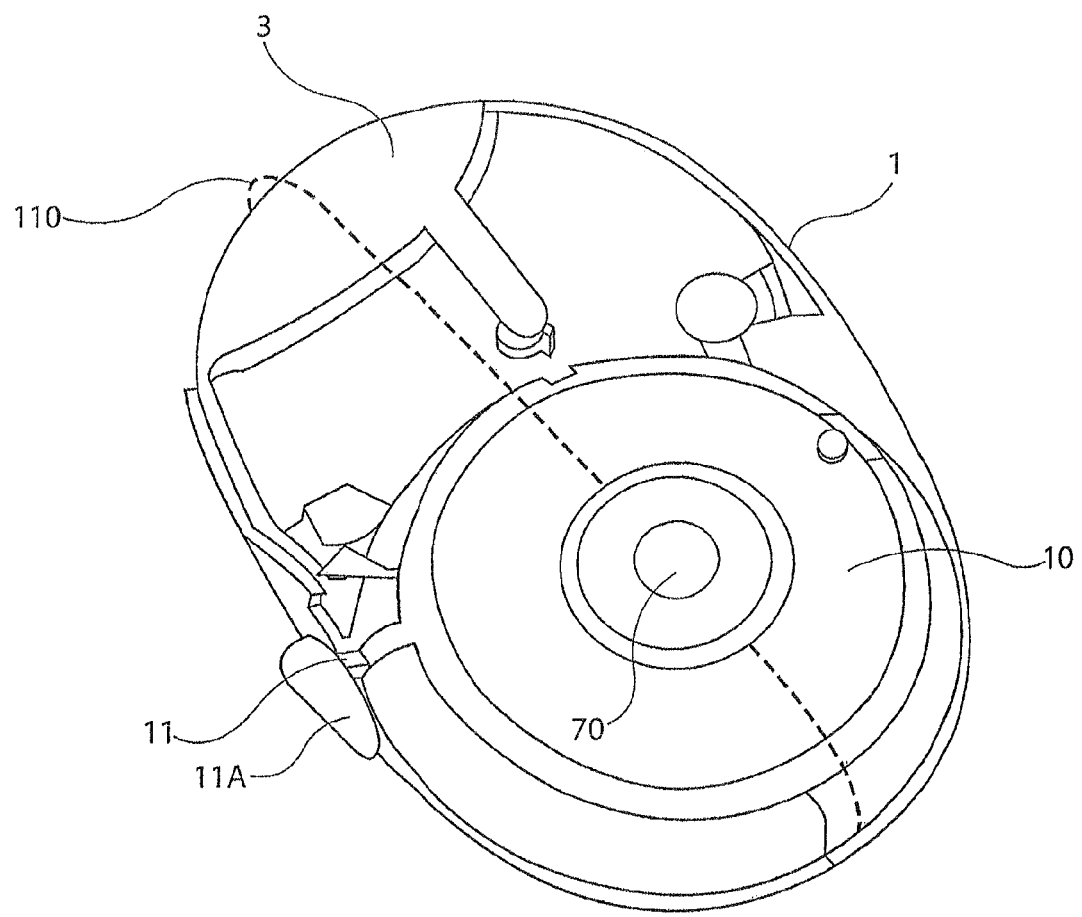
Figure 2B:
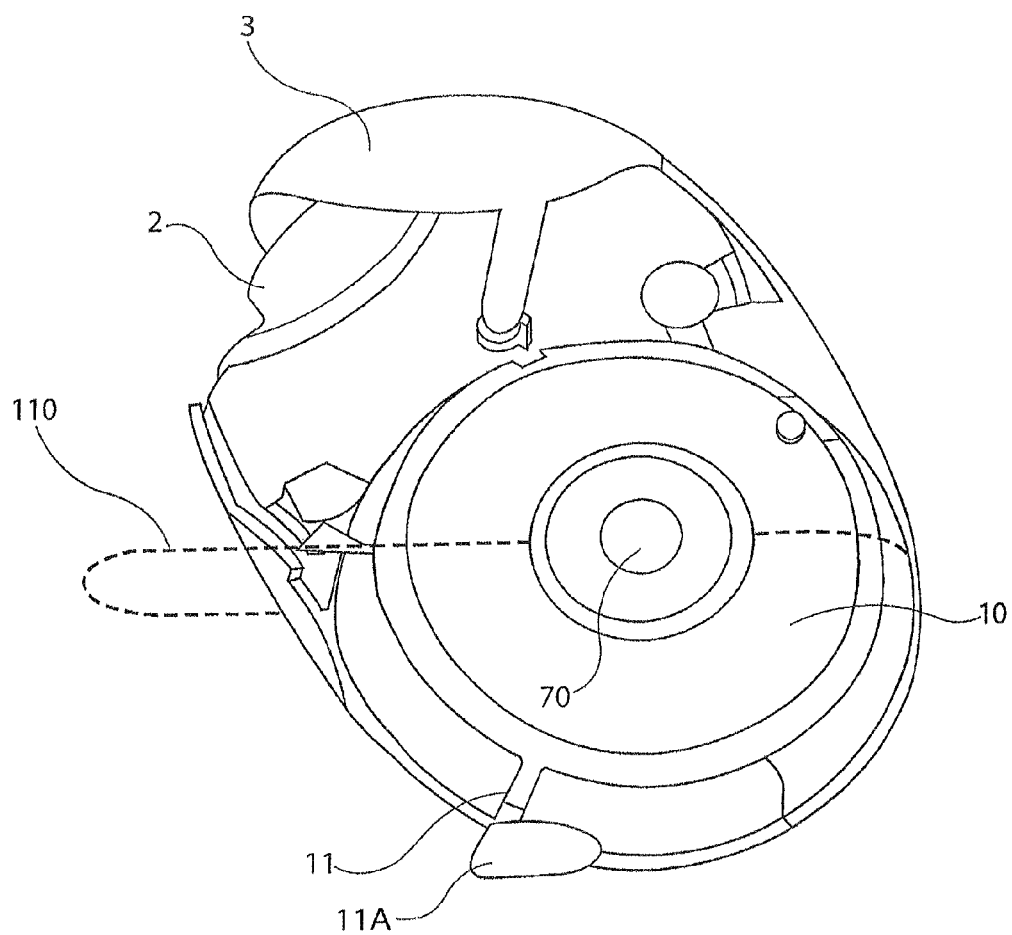
Figure 2C:
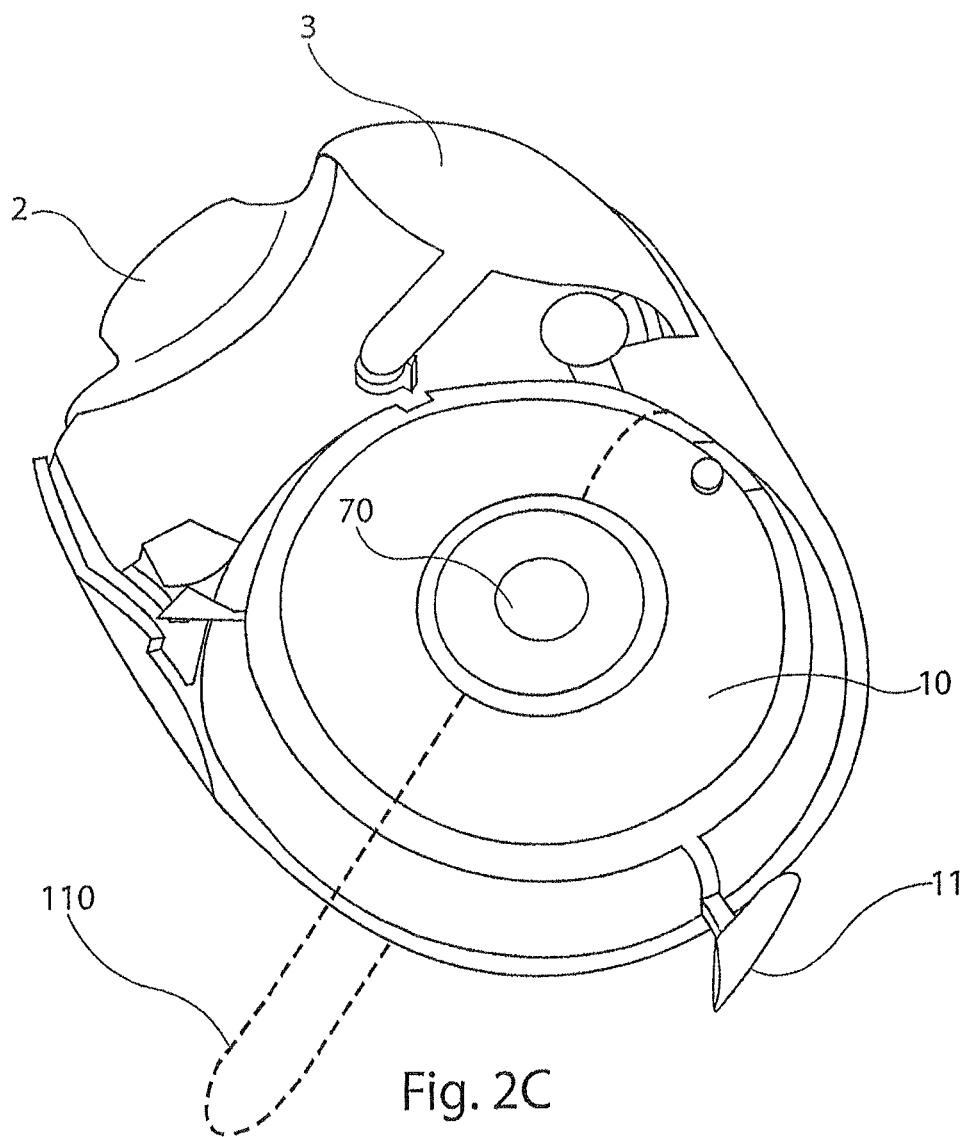

(52) U.S. Cl.
CPC ..... *A61M 2202/064* (2013.01); *A61M 2205/50* (2013.01); *A61M 2205/587* (2013.01); *A61M 2205/8206* (2013.01); *A61M 15/001* (2014.02); *A61M 15/0035* (2014.02); *A61M 15/0041* (2014.02); *A61M 15/0061* (2014.02); *A61M 15/0063* (2014.02); *A61M 15/0025* (2014.02)
USPC ............. 128/203.12; 128/203.15; 128/203.21

(56) References Cited

U.S. PATENT DOCUMENTS

| | | | |
|---|---|---|---|
| 3,518,992 A | 7/1970 | Altounyan et al. | |
| 3,635,219 A | 1/1972 | Altounyan et al. | 128/266 |
| 3,653,380 A | 4/1972 | Hansen | 128/203.15 |
| 3,795,244 A | 3/1974 | Lax et al. | 128/266 |
| 3,807,400 A | 4/1974 | Cocozza | 128/266 |
| 3,831,606 A | 8/1974 | Damani | 128/266 |
| 3,948,264 A | 4/1976 | Wilke et al. | 128/203.15 |
| 4,094,317 A | 6/1978 | Wasnich | 128/200.16 |
| 4,240,418 A | 12/1980 | Rosskamp et al. | 128/203.15 |
| 4,452,239 A | 6/1984 | Malem | 128/200.17 |
| 4,627,432 A | 12/1986 | Newell et al. | 128/203.15 |
| 4,733,797 A | 3/1988 | Haber | 221/8 |
| 5,152,284 A | 10/1992 | Valentini et al. | 128/203.21 |
| 5,260,321 A | 11/1993 | Hof et al. | 514/338 |
| 5,344,043 A | 9/1994 | Moulding et al. | 221/71 |
| 5,349,947 A | 9/1994 | Newhouse et al. | 128/203.21 |
| 5,429,302 A | 7/1995 | Abbott | 239/102.2 |
| 5,458,135 A | 10/1995 | Patton et al. | 128/200.14 |
| 5,497,763 A | 3/1996 | Lloyd et al. | 128/200.14 |
| 5,503,869 A | 4/1996 | Van Oort | 427/2.14 |
| 5,694,920 A * | 12/1997 | Abrams et al. | 128/203.15 |
| 5,699,649 A | 12/1997 | Abrams et al. | 53/428 |
| 5,709,202 A * | 1/1998 | Lloyd et al. | 128/200.14 |
| 5,724,959 A | 3/1998 | McAughey et al. | 128/203.15 |
| 5,727,546 A | 3/1998 | Clarke et al. | 128/203.15 |
| 5,740,793 A | 4/1998 | Hodson et al. | 128/203.15 |
| 5,758,823 A | 6/1998 | Glezer et al. | 239/4 |
| 5,823,178 A * | 10/1998 | Lloyd et al. | 128/200.14 |
| 5,823,434 A | 10/1998 | Cooper | 239/102.2 |
| 5,884,624 A | 3/1999 | Barnett et al. | 128/206.24 |
| 5,894,990 A | 4/1999 | Glezer et al. | 239/4 |
| 5,906,202 A | 5/1999 | Schuster et al. | 128/203.23 |
| 5,908,158 A | 6/1999 | Cheiman | 239/102.2 |
| 5,938,118 A | 8/1999 | Cooper | 239/102.2 |
| 6,026,809 A | 2/2000 | Abrams et al. | 128/203.15 |
| 6,032,666 A | 3/2000 | Davies et al. | 128/203.15 |
| 6,142,146 A | 11/2000 | Abrams et al. | 128/203.15 |
| 6,152,130 A | 11/2000 | Abrams et al. | 128/204.21 |
| 6,209,538 B1 | 4/2001 | Casper et al. | 128/203.15 |
| 6,312,909 B1 | 11/2001 | Shyjan | 435/6 |
| 6,328,033 B1 | 12/2001 | Avrahami | 128/203.15 |
| 6,347,629 B1 | 2/2002 | Braithwaite | 128/203.15 |
| 6,367,470 B1 | 4/2002 | Denyer et al. | 128/200.14 |
| 6,415,790 B1 | 7/2002 | Leedom et al. | 128/203.15 |
| 6,457,654 B1 | 10/2002 | Glezer et al. | 239/4 |
| 6,536,427 B2 | 3/2003 | Davies et al. | 128/203.15 |
| 6,543,442 B2 | 4/2003 | Gonda et al. | 128/200.14 |
| 6,546,927 B2 * | 4/2003 | Litherland et al. | 128/200.16 |
| 6,622,720 B2 | 9/2003 | Hadimioglu | 128/200.16 |
| 6,629,646 B1 | 10/2003 | Ivri | 239/4 |
| 6,698,425 B1 | 3/2004 | Widerstrom | 128/203.25 |
| 6,722,581 B2 | 4/2004 | Saddoughi | 239/102.2 |
| 6,759,159 B1 | 7/2004 | Gray et al. | 429/71 |
| 6,792,945 B2 | 9/2004 | Davies et al. | 128/203.15 |
| 6,840,239 B2 | 1/2005 | Myrman | |
| 6,871,647 B2 | 3/2005 | Allan et al. | 128/203.21 |
| 6,889,690 B2 | 5/2005 | Crowder et al. | 128/203.15 |
| 6,962,266 B2 | 11/2005 | Morgan et al. | 221/25 |
| 6,971,383 B2 | 12/2005 | Hickey et al. | 128/203.15 |
| 7,080,644 B2 | 7/2006 | Gumaste | 128/203.15 |
| 7,093,595 B2 * | 8/2006 | Nesbitt | 128/203.15 |
| 7,233,228 B2 | 6/2007 | Lintell | 340/309.7 |
| 7,318,434 B2 | 1/2008 | Gumaste et al. | 128/203.15 |
| 7,334,577 B2 | 2/2008 | Gumaste et al. | 128/203.15 |
| 7,451,761 B2 | 11/2008 | Hickey et al. | 128/203.21 |
| 7,538,473 B2 | 5/2009 | Blandino et al. | 310/317 |
| 7,607,435 B2 | 10/2009 | Lipp | 128/203.13 |
| 7,748,382 B2 | 7/2010 | Denyer et al. | 128/204.21 |
| 8,196,576 B2 | 6/2012 | Kriksunov et al. | 128/203.15 |
| 8,256,416 B2 | 9/2012 | Houzego et al. | 128/203.15 |
| 8,375,941 B2 | 2/2013 | King et al. | 128/203.15 |
| 8,763,606 B2 | 7/2014 | Mosier et al. | 128/203.15 |
| 2002/0032409 A1 | 3/2002 | Ritsche | 604/154 |
| 2003/0041859 A1 | 3/2003 | Abrams et al. | 128/200.22 |
| 2003/0192540 A1 | 10/2003 | Myrman et al. | 128/203.15 |
| 2004/0250812 A1 | 12/2004 | Davies et al. | 128/200.14 |
| 2004/0263567 A1 | 12/2004 | Hess et al. | 347/47 |
| 2005/0087189 A1 | 4/2005 | Crockford et al. | |
| 2005/0103337 A1 | 5/2005 | Hickey et al. | 128/203.15 |
| 2005/0109659 A1 | 5/2005 | Hickey et al. | 206/538 |
| 2005/0121027 A1 | 6/2005 | Nilsson et al. | 128/200.23 |
| 2005/0147566 A1 | 7/2005 | Fleming et al. | 424/46 |
| 2005/0155601 A1 | 7/2005 | Steiner et al. | 128/200.23 |
| 2005/0172962 A1 | 8/2005 | Gumaste et al. | |
| 2005/0174216 A1 | 8/2005 | Lintell | 340/309.16 |
| 2005/0183725 A1 | 8/2005 | Gumaste et al. | 128/203.15 |
| 2005/0267628 A1 | 12/2005 | Crowder et al. | 700/240 |
| 2005/0268909 A1 | 12/2005 | Bonney et al. | 128/203.15 |
| 2006/0174869 A1 | 8/2006 | Gumaste et al. | |
| 2006/0213503 A1 | 9/2006 | Borgschulte et al. | 128/200.14 |
| 2006/0257327 A1 | 11/2006 | Zierenberg et al. | 424/46 |
| 2007/0119969 A1 | 5/2007 | Collins et al. | 239/102.1 |
| 2007/0137645 A1 | 6/2007 | Eason et al. | 128/203.15 |
| 2007/0215149 A1 | 9/2007 | King et al. | 128/203.12 |
| 2008/0202514 A1 | 8/2008 | Kriksunov et al. | 128/203.15 |
| 2009/0020113 A1 | 1/2009 | Watanabe | 128/200.14 |
| 2009/0308390 A1 | 12/2009 | Smutney et al. | 128/203.15 |
| 2009/0314288 A1 | 12/2009 | Gumaste | 128/200.14 |
| 2010/0139654 A1 | 6/2010 | Thoemmes et al. | 128/203.15 |
| 2010/0252032 A1 | 10/2010 | Thoemmes et al. | 128/200.23 |
| 2011/0041844 A1 | 2/2011 | Dunne | 128/203.12 |
| 2013/0213392 A1 | 8/2013 | Mosier | 128/200.16 |

FOREIGN PATENT DOCUMENTS

| | | | |
|---|---|---|---|
| EP | 1 499 276 | 1/2005 | ............... A61J 7/00 |
| EP | 0 799 076 | 3/2005 | ............... A62B 18/00 |
| EP | 1 124 602 | 4/2005 | ............... A61M 11/06 |
| EP | 1 534 366 | 6/2005 | ............... A61M 15/00 |
| EP | 1 617 820 | 1/2006 | ............... A61K 47/18 |
| EP | 1 691 781 | 8/2006 | ............... A61J 1/00 |
| EP | 1 713 530 | 10/2006 | ............... A61B 5/08 |
| EP | 1 986 721 | 11/2008 | ............... A61M 15/00 |
| EP | 1 581 291 | 1/2009 | ............... A61M 15/00 |
| EP | 2 054 167 | 5/2009 | ............... B06B 1/02 |
| EP | 1 292 347 | 10/2009 | ............... A61M 15/00 |
| EP | 1 691 783 | 11/2009 | ............... A61K 9/14 |
| EP | 2 162 174 | 3/2010 | ............... A61M 15/00 |
| EP | 2 016 965 | 5/2010 | ............... A61M 11/00 |
| EP | 2 047 881 | 8/2010 | ............... A61M 15/00 |
| EP | 2 234 728 | 10/2010 | ............... A61M 15/00 |
| EP | 1 706 099 | 5/2011 | ............... A61K 9/14 |
| JP | H10-506028 | 6/1998 | |
| JP | 2007-520247 | 7/2007 | ............... A61M 15/00 |
| WO | WO96/06581 | 3/1996 | |
| WO | WO 97/26934 | 7/1997 | |
| WO | WO 98/32479 | 7/1998 | |
| WO | WO 99/64095 | 12/1999 | |
| WO | WO 99/65550 | 12/1999 | ............... A61M 15/00 |
| WO | WO 03/092576 | 11/2003 | ............... A61J 7/04 |
| WO | WO 2004/002394 | 1/2004 | |
| WO | WO 2004/093848 | 11/2004 | ............... A61K 9/16 |
| WO | WO 2005/053646 | 6/2005 | ............... A61K 9/14 |
| WO | WO 2005/074455 | 8/2005 | |
| WO | WO 2007/096111 | 8/2007 | ............... A61M 15/00 |
| WO | WO 2008/021281 | 2/2008 | |
| WO | WO 2008/106616 | 9/2008 | ............... A61M 16/00 |
| WO | WO 2009/007068 | 1/2009 | ............... A61M 15/00 |
| WO | WO 2009/090084 | 7/2009 | ............... A61M 15/00 |
| WO | WO 2010135672 | 11/2010 | ............... A61M 15/00 |

(56) References Cited

FOREIGN PATENT DOCUMENTS

| WO | WO 2011/160932 | 12/2011 | ............ A61M 15/00 |
| WO | WO 2011/163272 | 12/2011 | ............ A61M 15/00 |

OTHER PUBLICATIONS

International Search Report and Written Opinion, Jul. 21, 2010.
New Zealand Examination Report, Patent Appln. No. 596564, dated Oct. 2, 2012, 2 pages.
Eurasian Office Action (w/translation) issued in related application No. 201171452, dated Nov. 1, 2013 (2 pgs).
Chinese Third Office Action (w/translation) issued in related application No. 201080022180.3, dated Dec. 31, 2013 (14 pgs).
Australian Patent Examination Report No. 1 issued in related application No. 2010249402, dated Jan. 10, 2014 (3 pgs).
Office Action issued in related U.S. Appl. No. 12/785,082, dated Oct. 23, 2013 (35 pgs).
Second Chinese Office Action issued in corresponding application No. 201080022180.3, dated Jul. 11, 2013 (9 pgs).
Official Action and translation issued in corresponding Chilean case Appln. No. 2900-2011, dated Oct. 2, 2013 (15 pgs).
Australian Patent Examination Report No. 2 issued in corresponding Australian Patent Serial No. 2010249402 dated Mar. 3, 2014 (3 pgs).
Translation of Japanese Action issued in related Japanese Patent Appln. Serial No. 2012-512067 dated Feb. 27, 2014 (2 pgs).
Japanese Decision of Refusal (with translation) issued in related application No. 2012-512067, dated Jun. 23, 2014 (4 pgs).
Mexican Office Action (with translation) issued in related application No. MX/a/2011/012265, dated Apr. 10, 2014 (5 pgs).
Notice of Allowance issued in related U.S. Appl. No. 12/785,082, dated May 9, 2014 (33 pgs).
Eurasian Office Action (with translation) issued in related application No. 201171452, dated Sep. 4, 2014 (4 pgs).
Indonesian Office Action (no translation) issued in related application No. W-00201104678, dated Oct. 2, 2014 (2 pgs).

* cited by examiner

METHOD AND DEVICE FOR CLAMPING A BLISTER WITHIN A DRY POWDER INHALER

CROSS REFERENCE TO RELATED APPLICATION

This application is a continuation in part of U.S. application Ser. No. 12/785,082, filed May 21, 2010, which claims priority from the U.S. Provisional Application Ser. No. 61/180,396, filed May 21, 2009, the contents of which are incorporated herein in their entireties, by reference.

FIELD OF THE INVENTION

The present disclosure relates generally to the field of inhalation devices. The disclosure has particular utility in connection with the delivery of powdered medications to a patient, and will be described in connection with such utility, although other utilities are contemplated.

BACKGROUND OF THE INVENTION

Certain diseases of the respiratory tract are known to respond to treatment by the direct application of therapeutic agents. As these agents are most readily available in dry powdered form, their application is most conveniently accomplished by inhaling the powdered material through the nose or mouth. This powdered form results in the better utilization of the medicament in that the drug is deposited exactly at the site desired and where its action may be required; hence, very minute doses of the drug are often equally as efficacious as larger doses administered by other means, with a consequent marked reduction in the incidence of undesired side effects and medicament cost. Alternatively, the drug in this form may be used for treatment of diseases other than those of the respiratory system. When the drug is deposited on the very large surface areas of the lungs, it may be very rapidly absorbed into the blood stream; hence, this method of application may take the place of administration by injection, tablet, or other conventional means.

It is the opinion of the pharmaceutical industry that the bioavailability of the drug is optimum when the drug particles delivered to the respiratory tract are between 1 to 5 microns in size. When the drug particles need to be in this size range the dry powder delivery system needs to address a number of issues:

(1) Small size particles may develop an electrostatic charge on themselves during manufacturing and storage. This may cause the particles to agglomerate or aggregate, resulting in clusters of particles which have an effective size greater than 5 microns. The probability of these large clusters making it to the deep lungs then decreases. This in turn results in a lower percentage of the packaged drug being available to the patient for absorption.

(2) The amount of active drug that needs to be delivered to the patient may be of the order of 10 s of micrograms. For example, in the case of albuterol, a drug used in asthma, this is usually 25 to 50 micrograms. Current manufacturing equipment can effectively deliver aliquots of drugs in milligram dose range with acceptable accuracy. So the standard practice is to mix the active drug with a filler or bulking agent such as lactose. This additive also makes the drug "easy to flow". This filler is also called a carrier since the drug particles also stick to these particles through electrostatic or chemical bonds. These carrier particles are very much larger than the drug particles in size. The ability of the dry powder inhaler to separate drug from the carrier is an important performance parameter in the effectiveness of the design.

(3) Active drug particles with sizes greater than 5 microns will be deposited either in the mouth or throat. This introduces another level of uncertainty since the bioavailability and absorption of the drug in these locations is different from the lungs. Dry powder inhalers need to minimize the drug deposited in these locations to reduce the uncertainty associated with the bioavailability of the drug.

Prior art dry powder inhalers (DPIs) usually have a means for introducing the drug (active drug plus carrier) into a high velocity air stream. The high velocity air stream is used as the primary mechanism for breaking up the cluster of micronized particles or separating the drug particles from the carrier. Several inhalation devices useful for dispensing this powder form of medicament are known in the prior art. For example, in U.S. Pat. Nos. 3,507,277; 3,518,992; 3,635,219; 3,795,244; and 3,807,400, inhalation devices are disclosed having means for piercing of a capsule containing a powdered medicament, which upon inhalation is drawn out of the pierced capsule and into the user's mouth. Several of these patents disclose propeller means, which upon inhalation aid in dispensing the powder out of the capsule, so that it is not necessary to rely solely on the inhaled air to suction powder from the capsule. For example, in U.S. Pat. No. 2,517,482, a device is disclosed having a powder containing capsule placed in a lower chamber before inhalation, where it is pierced by manual depression of a piercing pin by the user. After piercing, inhalation is begun and the capsule is drawn into an upper chamber of the device where it moves about in all directions to cause a dispensing of powder through the pierced holes and into the inhaled air stream. U.S. Pat. No. 3,831,606 discloses an inhalation device having multiple piercing pins, propeller means, and a self-contained power source for operating the propeller means via external manual manipulation, so that upon inhalation the propeller means aids in dispensing the powder into the stream of inhaled air. See also U.S. Pat. Nos. 3,948,264 and 5,458,135.

In prior U.S. Pat. Nos. 7,318,434 and 7,334,577 incorporated herein by reference, and assigned to the common assignee MicroDose Therapeutx, Inc., there is provided an improvement over prior art inhalers that utilize vibration to facilitate suspension of power into an inhaled gas stream and which utilizes synthetic jetting to aerosolize drug powder from a blister pack or the like. As taught in the aforesaid U.S. Pat. Nos. 7,318,434 and 7,334,577 there is provided a dry powder inhaler having a first chamber such as a blister pack or other container, for and holding a dry powder, and a second chamber connected to the first chamber via a passageway for receiving an aerosolized form of the dry powder from the first chamber and for delivering the aerosolized dry powder to a user. A vibrator is coupled to the dry powder in the first chamber. The vibrator is energized and coupled to the first chamber and drives the powder from the chamber by synthetic jetting.

As described in U.S. Pat. No. 7,080,644 also incorporated herein by reference, and also assigned to common assignee MicroDose Therapeutx, Inc., controlled aliquots or doses of a medication or drug are pre-packaged in a blister pack, which includes a frangible crowned top element which may be conical, conical with a rounded point, rounded, or other raised shape configuration, and a bottom element which may be a flat web or membrane, or which itself may be of shaped configuration, e.g. conical, round, dish shaped, etc. for closely engaging with an underlying vibrating element, the shape and size of which is chosen to provide optimum controlled delivery of a given medication or drug. The top element of the blister pack is pierced with a piercing device such as a sharp needle to form one or more apertures for delivery of the medication or drug contained within the blister pack. The hole pattern and hole size is selected to provide optimization of delivery of the particular medication or drug packaged therein.

SUMMARY OF THE INVENTION

The present disclosure provides an improvement over the prior art devices such as discussed above by providing an inhaler having a vibration element for aerosolizing medicament contained in a blister pack, wherein the inhaler is adapted to hold a plurality of individual blister packs which can be individually accessed and moved into an operative or dispensing position between the vibration element and a piercing element. The advantages of this construction include: simpler, more compact assembly for an inhaler containing a plurality of blister packs; and the ability to isolate and shield individual blister packs from the piercing element prior to use.

One aspect of the present disclosure provides a medication inhaler, with a housing, including a vibrating element. The housing also includes a chamber-defining flow-channel wherein a blister containing medicament is clamped in place by the chamber. The blister is also in contact with the vibrating element. The positioning is accomplished by a blister pack clamping surface, allowing three rotational degrees of freedom between the chamber and blister pack, and allowing the crown of the blister to be engaged at least in part with the chamber.

BRIEF DESCRIPTION OF THE DRAWINGS

Further features and advantages of the present disclosure will be seen from the following detailed description, taken in conjunction with the accompanying drawings, wherein FIGS. 1A and 1B are top views of an inhaler according to the present disclosure, displaying different positions of the lever arm;

FIGS. 2A, 2B, and 2C are sectioned views of an inhaler with a rotary cassette activated by a lever aim in accordance with the present disclosure;

FIG. 3 is an exploded view of a cartridge assembly in accordance with the present disclosure;

FIG. 4 is an illustration of a cartridge assembly being loaded into the housing of an inhaler of the present disclosure;

FIG. 5 is an illustration showing the bottom of an inhaler in accordance with the present disclosure;

FIG. 6A is an illustration of a blister pack in accordance with the present disclosure;

FIG. 6B is an illustration showing the operation of a blister pack carrier in accordance with the present disclosure;

FIG. 7 is a partial view of the internal elements of the dry powder inhaler of the present disclosure;

FIGS. 8*a* and 8*b* are detailed sectional views of the blister pack carrier and piercing mechanism in accordance with the present disclosure;

FIGS. 9A and 9B are detailed section views of the flow channel and the vibrating and piercing elements of the present disclosure;

FIG. 10 is a block diagram showing the operation of the electronics associated with the dry powder inhaler of the present disclosure;

FIG. 11 is an illustration of a printed circuit carrier in accordance with the present disclosure;

FIG. 12 is a sectioned side view of a dry powder inhaler in accordance with the present disclosure;

FIG. 13 is an exploded view of a dry powder inhaler in accordance with the present disclosure;

FIG. 14 is a sectioned side view of a blister engaged with a vibrating element in accordance with the present disclosure; and FIG. 15 is a sectioned side view of a blister engaged with a vibrating element in accordance with another embodiment of the present disclosure.

DETAILED DESCRIPTION OF PREFERRED EMBODIMENTS

In the following description, reference is made to the accompanying drawings, which form a part hereof, and in which is shown, by way of illustration, various embodiments of the present disclosure. It is understood that other embodiments may be utilized and changes may be made without departing from the scope of the present disclosure.

The present disclosure provides a device for delivering medicament to the airway of a user, wherein the device generally comprises a housing with a mouthpiece affixed and a cover for the mouthpiece. The housing is adapted to hold a plurality of individual blister packs containing, for example, powdered medicament. However, the medication could be a liquid form medication. The blisters are arranged such that individual blisters may be loaded into a clamping position, whereupon the blister is pierced and a vibrating device is used to aggregate the contents of the blister, which is subsequently inhaled by the user. Preferably the blisters are carried in a cartridge which in a preferred form comprises a rotary cassette containing a plurality of individually addressable blister packs. The device also includes a mechanism for moving selected blister packs between a stowed position and an operative position. The mechanism may also be used to activate the piercing and vibrating elements.

Referring to FIGS. 1A and 1B, the inhaler of the present disclosure comprises a housing 1 having a mouthpiece 2, and a retractable cover 3. The device may also include a lever arm 11, the movement of which opens the retractable cover and activates other elements of the device, as will be described in detail below. The retractable cover may also be opened manually, such as when the user desires to clean the mouthpiece, but may not be closed when the lever arm 11 has been moved to an open position.

Referring to FIGS. 2A-2C, the lever arm 11 is connected to a cam disk 10 contained within the housing which translates the rotational motion of the lever arm to translational or rotational motion of other internal elements of the device. The device as shown is configured to allow the lever arm to turn 120°, which is a convention range of motion for operating the device with one hand, but other ranges are also possible. As the lever arm progresses from one position to another (see FIGS. 2A-2C), cam disk 10 is turned and retractable cover 3 uncovers the mouthpiece 2. The rotation of the cam disk is shown by reference line 110.

The distal end of the lever arm (relative to the cam disk) forms a button area 11A that is configured to allow a user to easily grip and move the lever arm. For example, the surface area of the button should be large enough to allow easy pulling of the lever arm and the surface of the button may also be comprised of a material that enhances the grip of the user. At either end of the motion of the lever arm, the device may include a sequence lock that allows the lever arm and cam disk to remain in a fixed position until the user moves the lever arm again.

Alternatively, other motions may be used to activate the device. For example, the cover of the device may be connected to the cam disk by a linkage that turns the cam disk when the cover is opened.

Referring to FIGS. 1A and 1B and 2A-2C, the device also includes an indicator 70 that communicates information to the user that may include, for example, a reminder when a new dose is to be administered, an indication of when the user should inhale, an indication of when the user should be done inhaling, and a warning, for example, when the device is empty, the medication is out of date, or the device was subject to environmental extremes, e.g. heating or cooling, beyond its design range. The device should indicate the inhale signal to the user when a blister pack has been opened and can no longer be stored. A ratcheting feature may also be incorporated into the cam disk 10 to prevent partial or accidental activation of the device.

Figure 3:
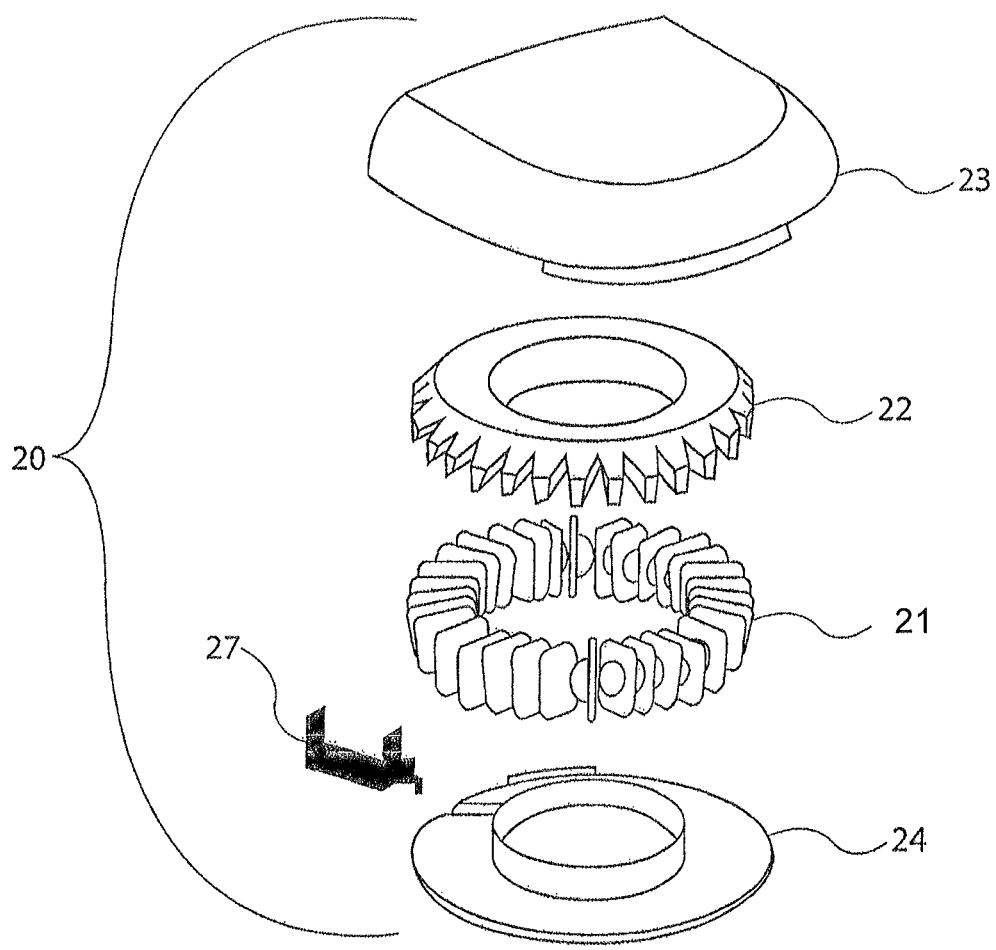

FIG. 3 shows the different pieces of the cartridge assembly of the present disclosure. The cartridge 20 containing the rotary cassette is generally arranged such that the plurality of individual blister packs 21 are fanned out in a radial pattern relative to the plane of the rotary cassette. FIG. 3 shows one cartridge comprising an upper housing 23 and a lower housing 24. The cartridge contains a blister carousel 22 that separates each of the blister packs 21. The cartridge also includes a blister carrier 27 that is used to move one blister pack at a time along a radial path into an operating position. The cartridge can be configured to carry a wide range of number of blister packs.

Figure 4:
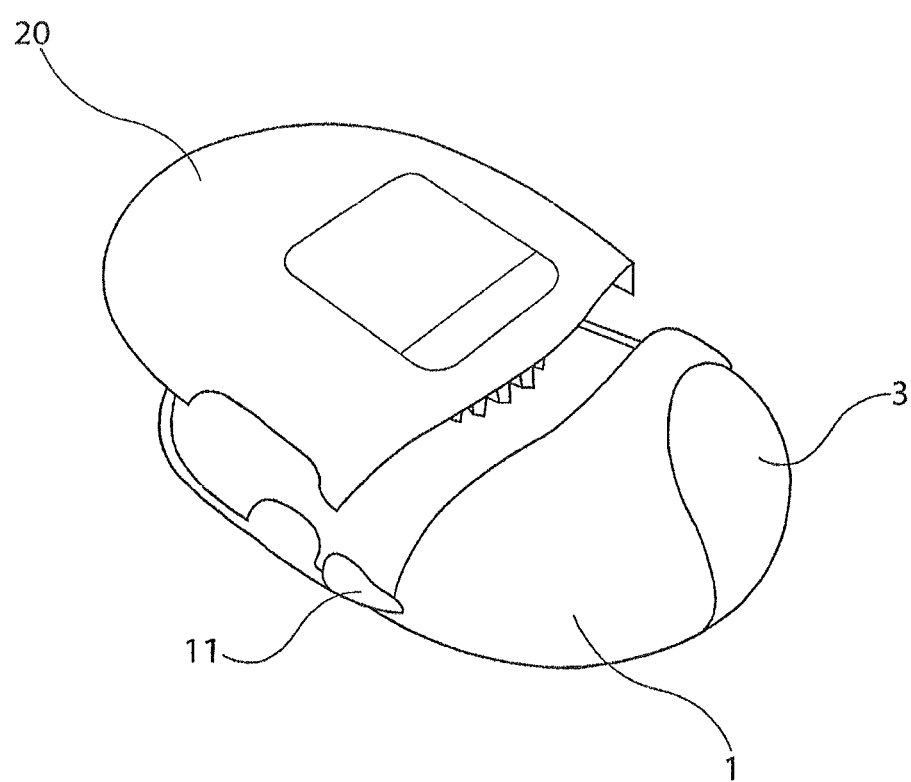
Figure 5:
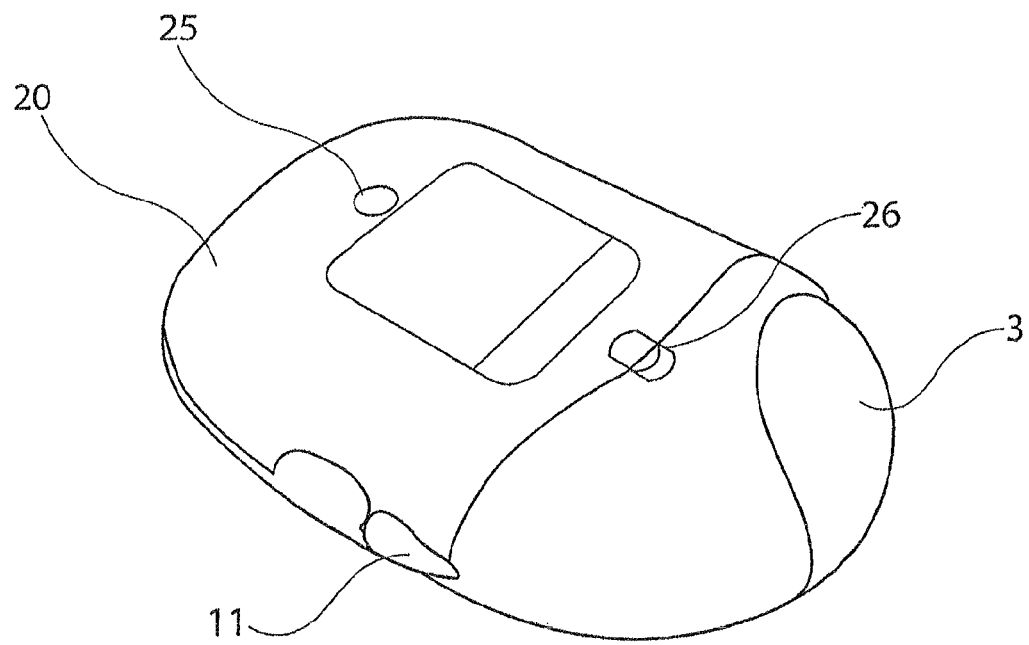

As shown in FIG. 4, the cartridge may be removed and reloaded or replaced so that the device may continue to be used. FIG. 5 shows that the cartridge may also include a dose counter 25 for tracking the number of doses, and a release tab 26 to facilitate removal of the cartridge.

Figure 6A:
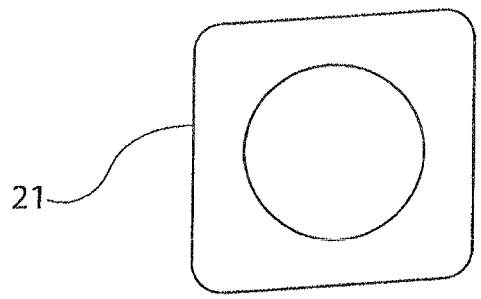

FIG. 6A shows a typical blister pack. Other blister pack designs are also possible. For examples of other blister pack designs that may be compatible with the device of the present disclosure, see, for example, U.S. Published Application Nos. 2006/0174869 A1, now U.S. Pat. No. 7,334,577, 2008/0202514A1, and 2009/0314288 A1, all assigned to a common assignee and incorporated by reference herein. Alternatively, the blister packs may comprise a divided package or blister pack containing two or more medicaments or drugs, e.g. of the same or different particle size, for co-delivery to a user as disclosed, e.g. in U.S. Published Application No. 2005/0147566 A1, also assigned to a common assignee.

Figure 6B:
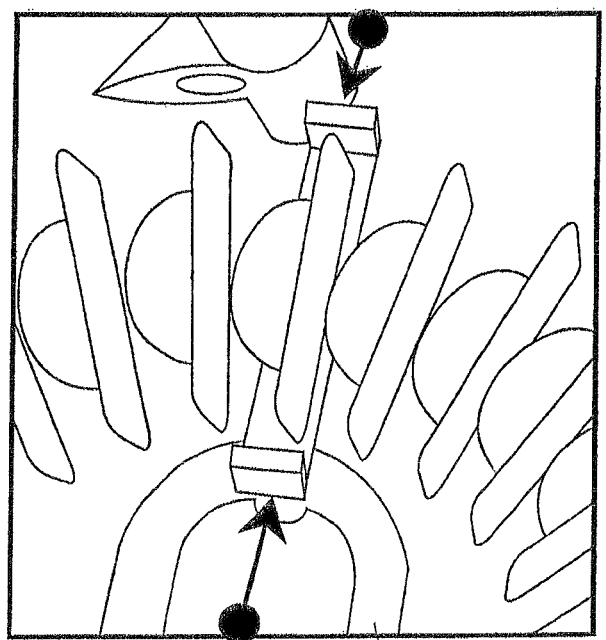

As described above, the medicament or drug contained in the blister pack is delivered to the patient by pushing a fresh blister pack 21 into position using blister carrier 27. The motion of the blister carrier is in a radial direction, as indicated by the arrows in FIG. 6B.

Figure 7:
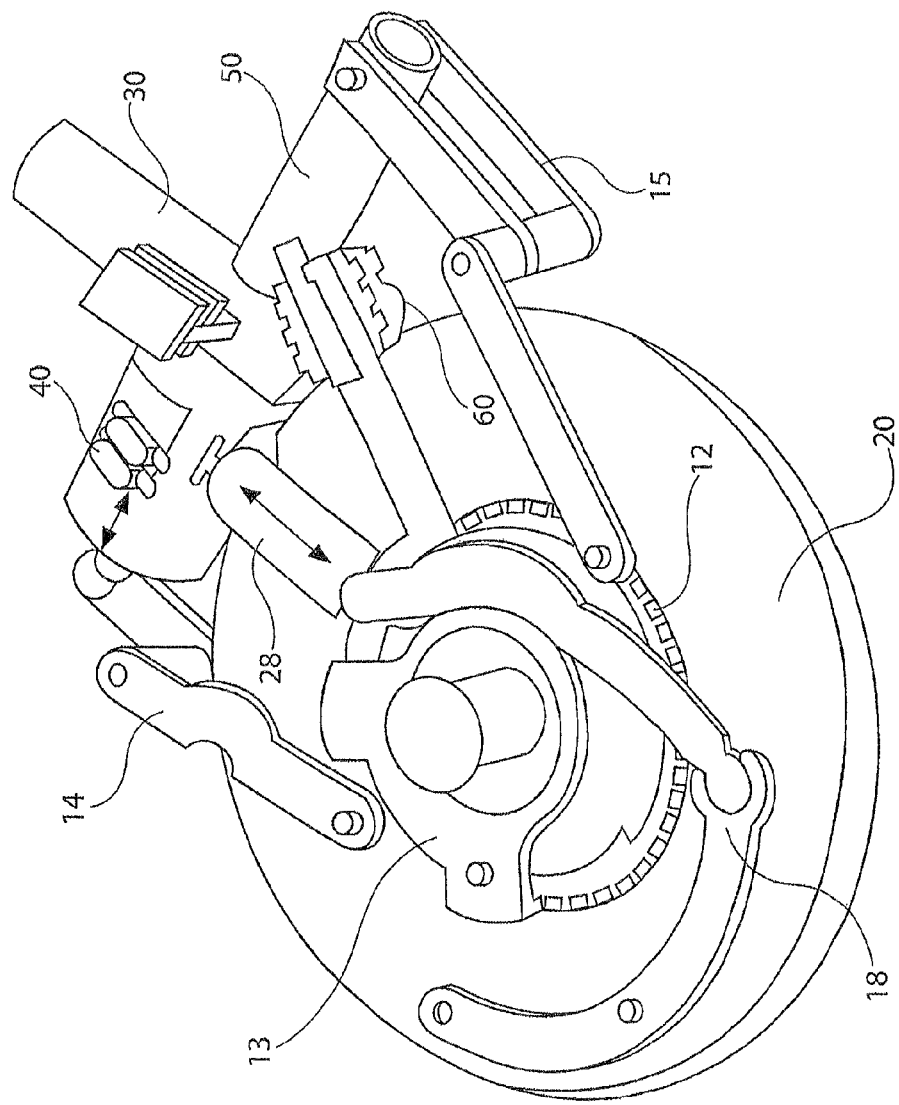
Figure 8A:
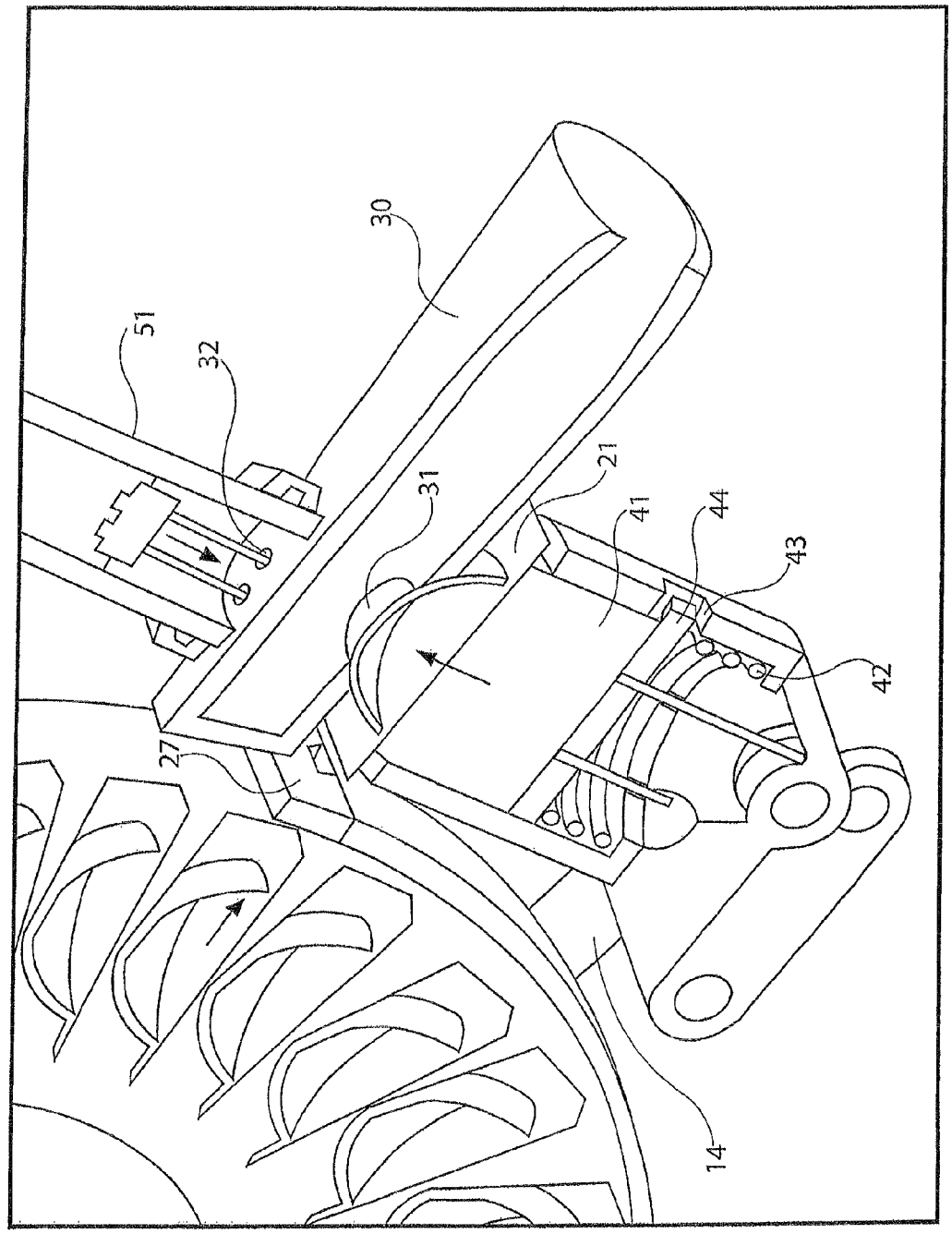
Figure 8B:
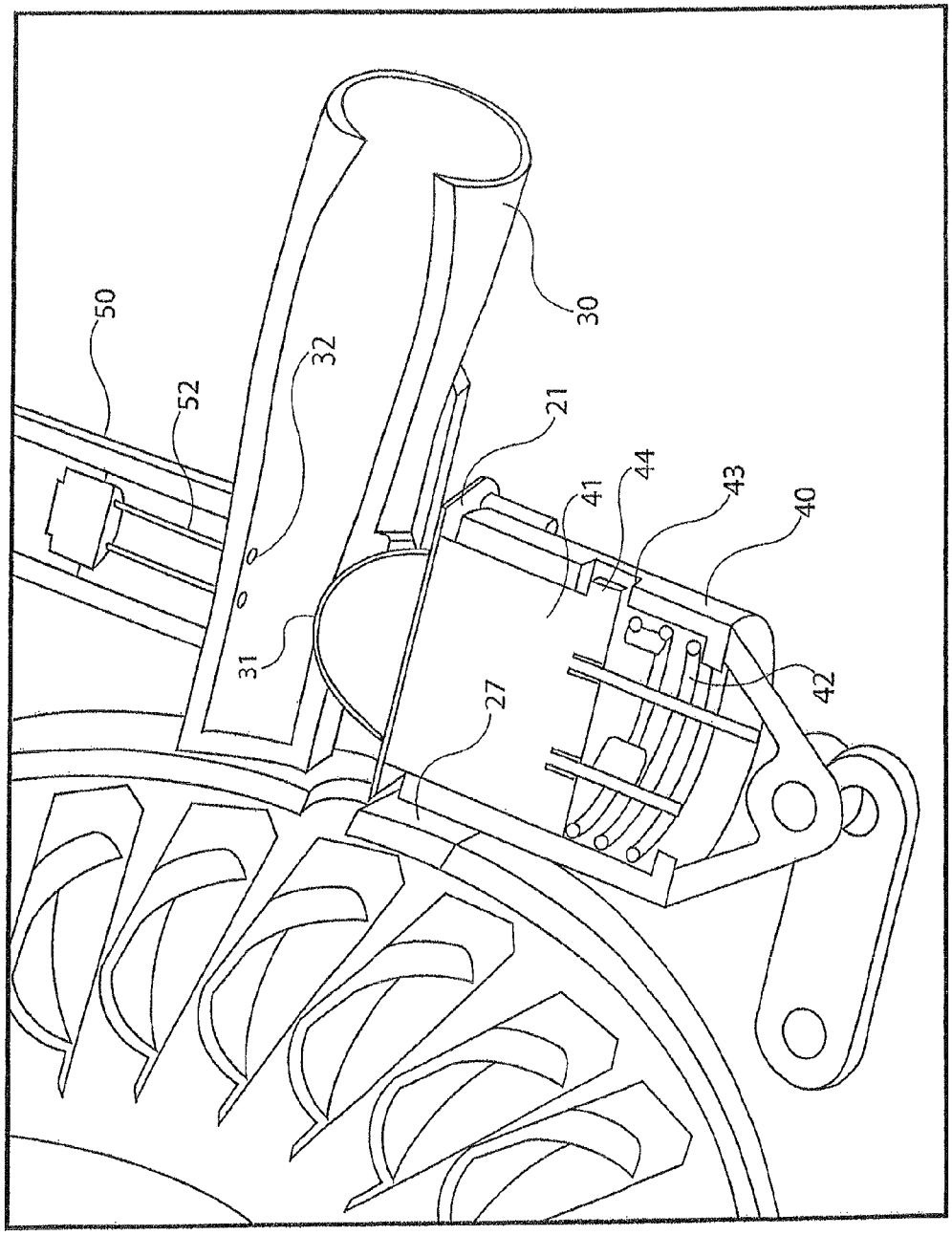
Figure 9A:
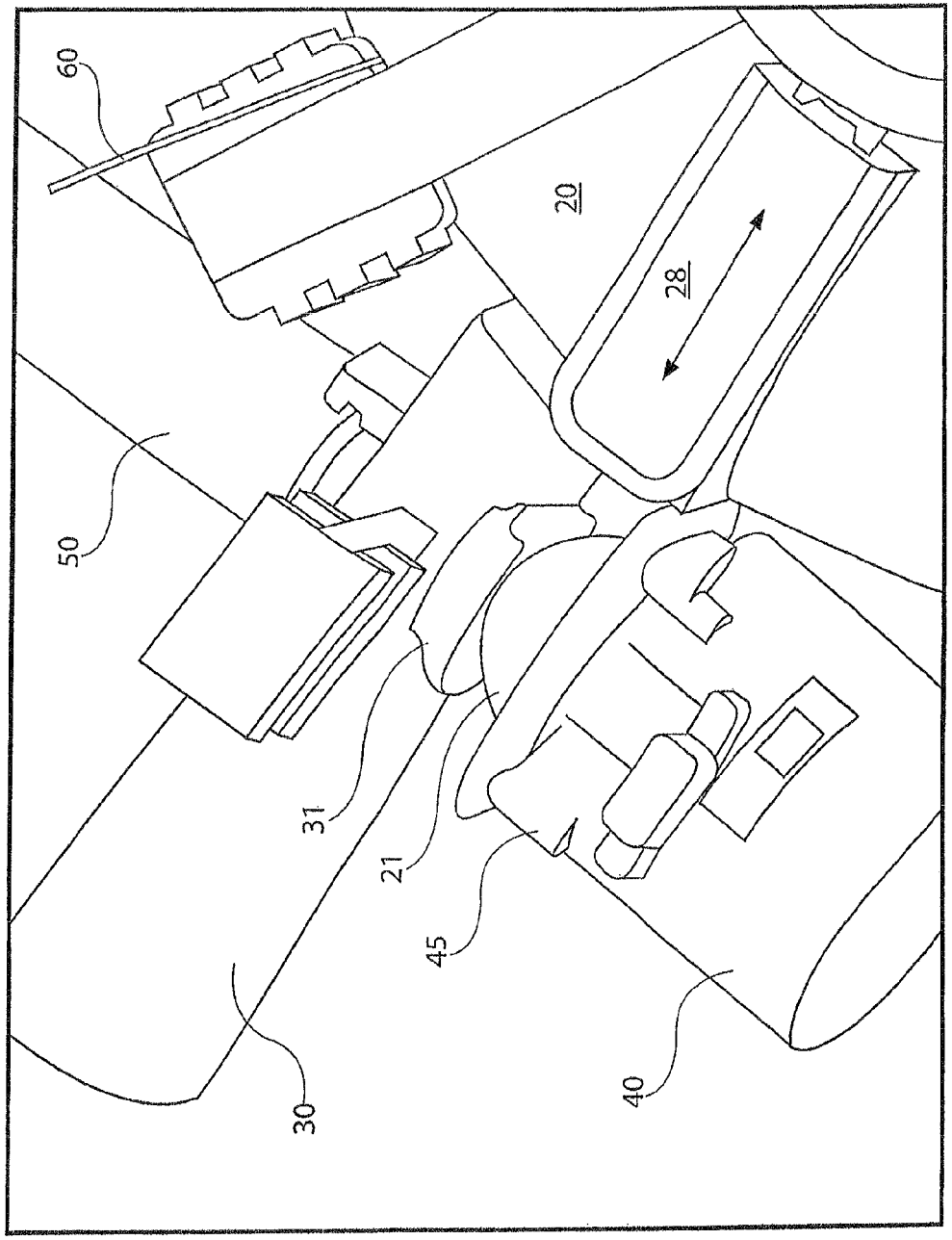
Figure 9B:
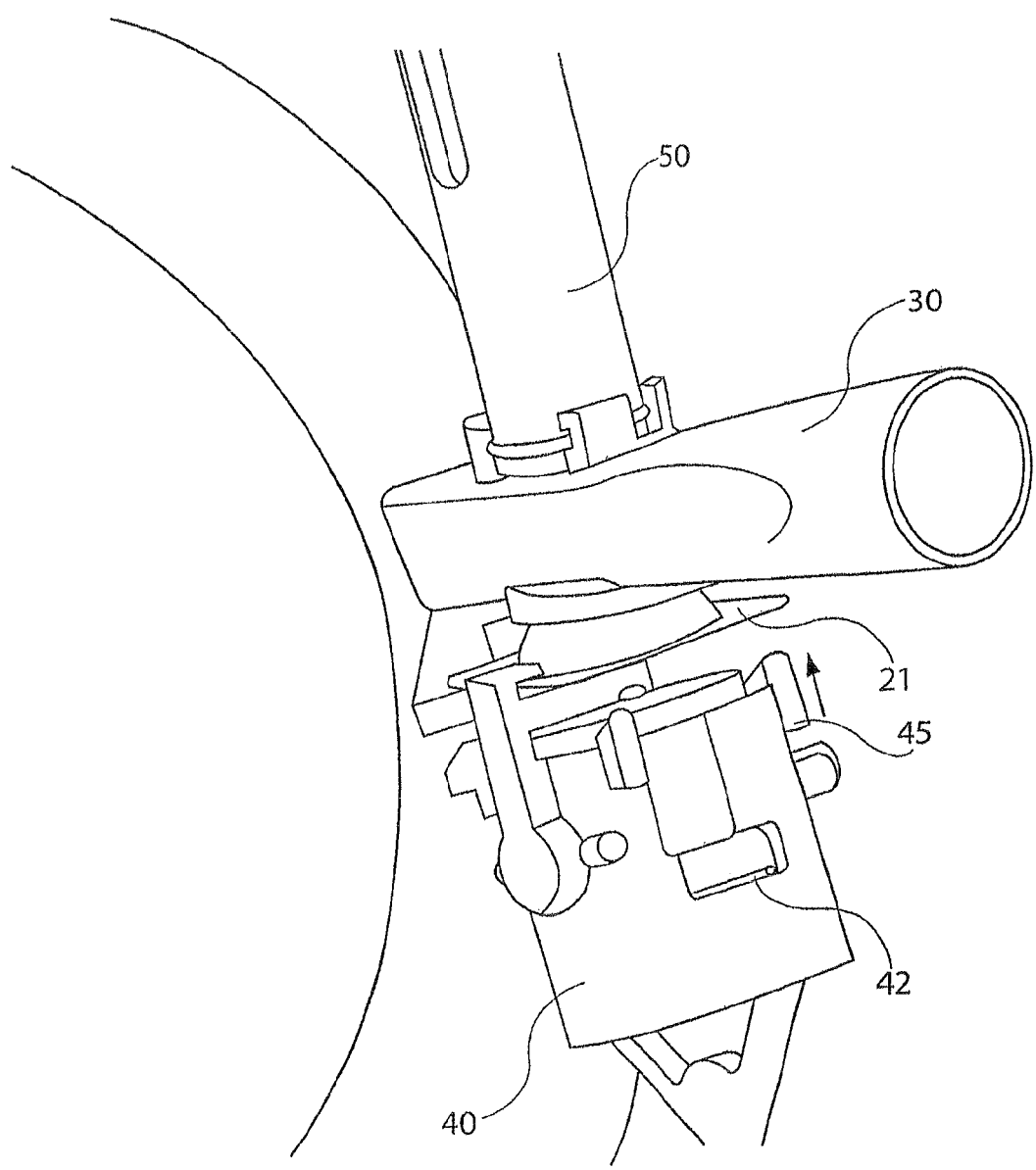
Figure 10:
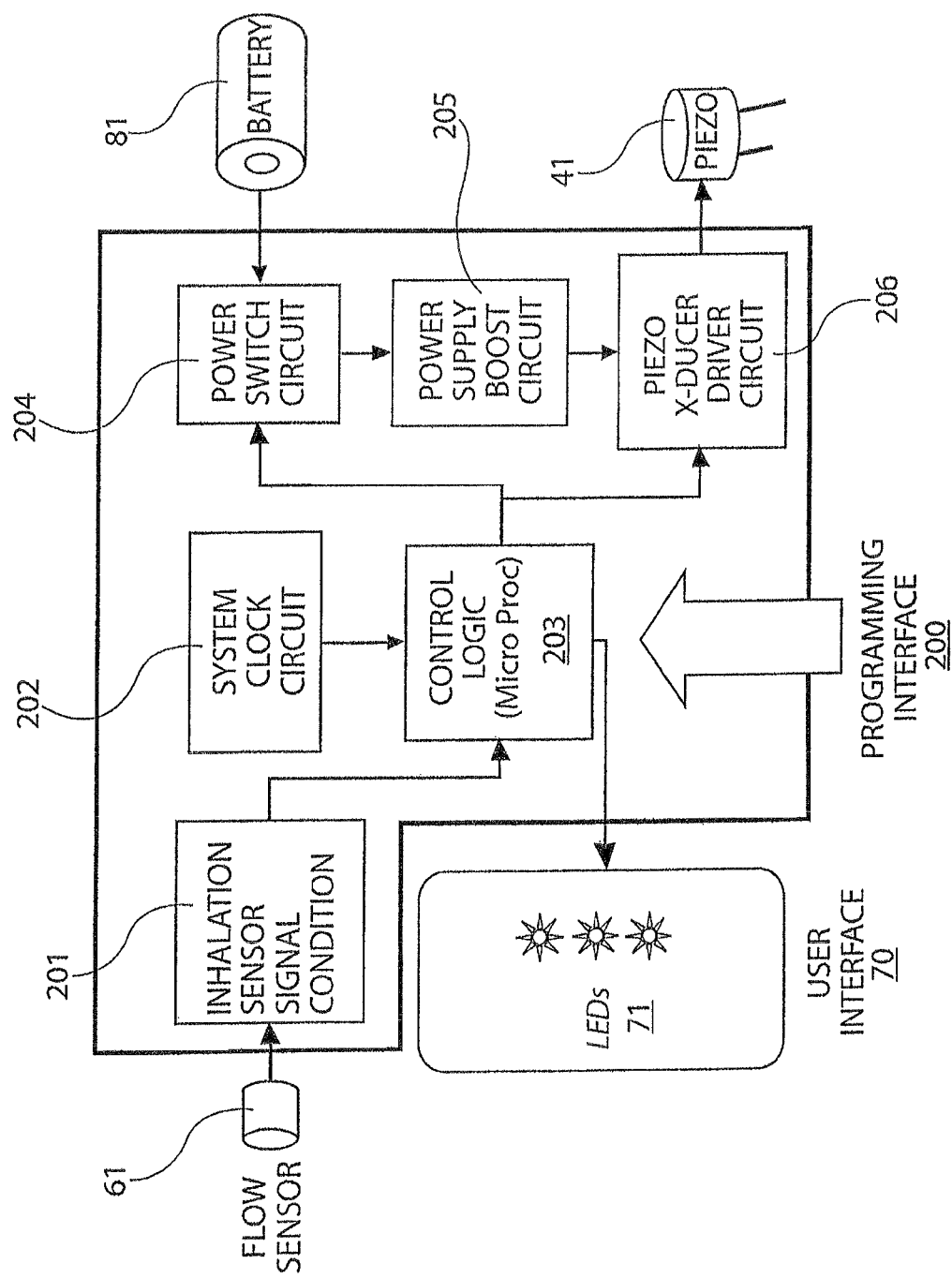
Figure 11:
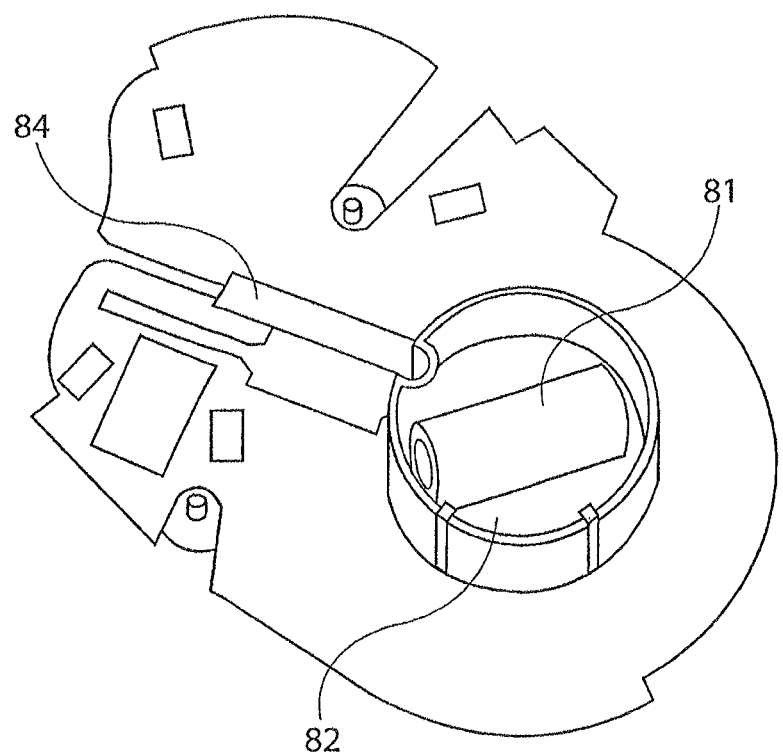
Figure 12:
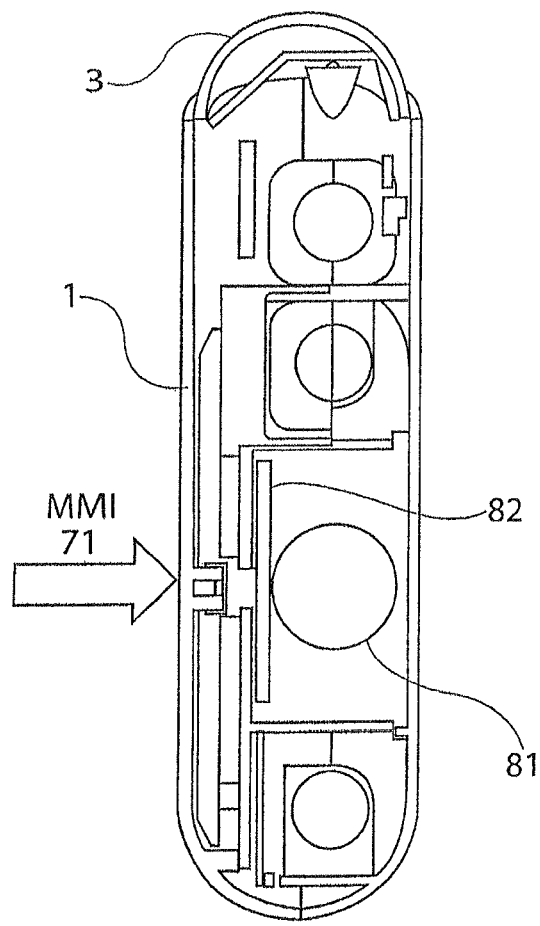

Motion of the blister carrier, as well as the retractable cover is initiated by the movement of the lever arm 11, the rotational motion of which is transferred to other respective elements using cam disk 10, which includes a series of slots, cams, and/or pins that control the movement of linkages connected to other elements of the device. These connections are demonstrated by FIG. 7, which shows the disposition of the various linkages in connection with the cartridge assembly 20, the vibrator assembly 40, and the piercing assembly 50. (The cam disk is not shown in this view). The cam disk connects to a cartridge index linkage 13 that turns the cartridge making the next blister pack available after each time the device is used; a blister transport linkage 18 that is connected to blister transport sled 28, which in turn is connected to blister carrier 27; and a vibrator linkage 14; a piercing linkage 15. The cartridge assembly further includes ratchet teeth 12 that enable the indexing feature. The linkages as shown here are merely exemplary. Several other configurations are also possible. For instance, the length and number of linkages may be changed while still achieving a similar result.

Where cams, slots and follower pins, rotating pins, or other pieces conflict with one another, the cam disk 10 may comprise of two flat inner and outer disks joined together, such as for example, being joined at a hub. In this manner, the disk may include overlapping slots or cams.

Referring to FIGS. 8A, 8B, 9A, and 9B, the blister carrier 27 moves a selected blister pack 21 into position between the piercing assembly 50 and the vibrating assembly 40. The top of the blister extends through opening 31 into flow channel 30, which is connected to mouthpiece 2. The blister pack is clamped in place by the vibrator assembly 40 which includes spring 42 for placing piezoelectric transducer 41 against blister pack and holding the blister pack in place. Posts 45 may be provided to ensure that proper contact between the vibrating element and the blister pack is maintained. Alternatively, the opening 31 in the flow channel 30 may be made large enough to allow the blister pack to extend further into the flow channel, wherein flange area of blister pack 21 is clamped between the piezoelectric transducer and the flow channel. Slot 43 is aligned with protrusion 44, limiting the range of motion of the spring 42.

The piercing assembly is aligned with the blister pack on the opposite side of the flow channel with the piercer 51 extending through holes 32 when used to puncture the blister pack. The piercer may comprise a needle or plurality of needles to adequately puncture the blister pack.

Figure 13:
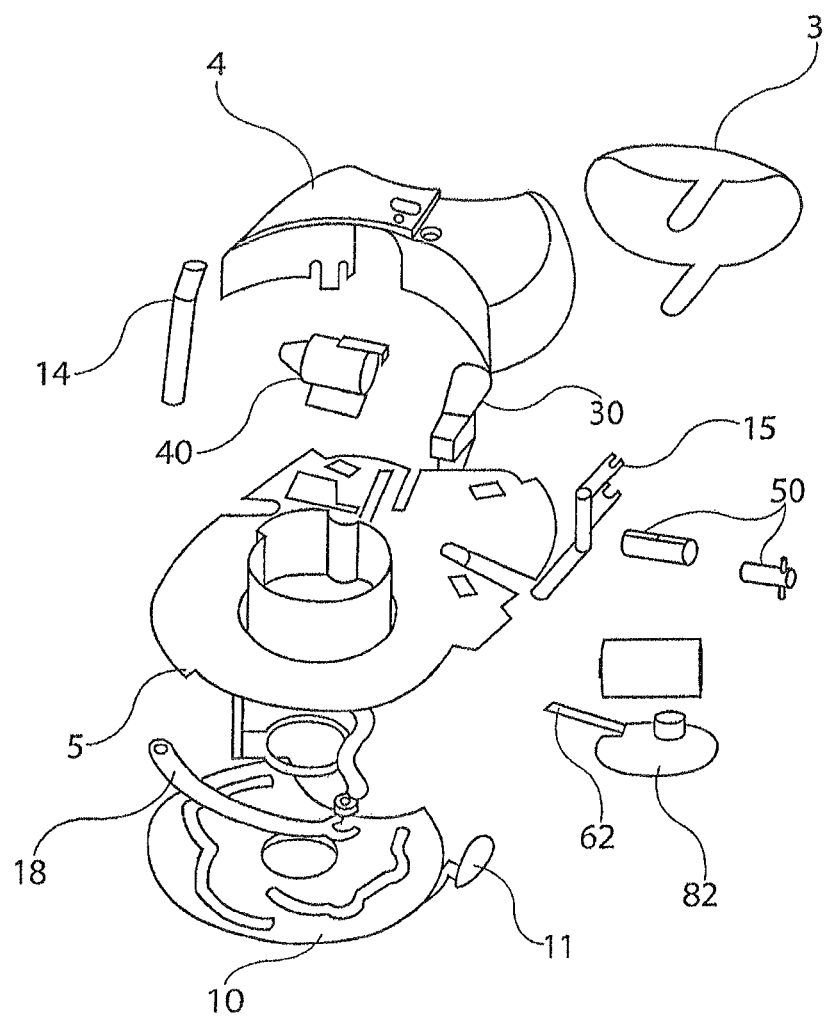

The vibrating assembly 40 may include a piezoelectric transducer 41 as a vibrating element, but other vibrating elements are also within the scope of the present disclosure, such for example as a microphone providing a sonic vibration. The vibrating element causes the powdered medicament within the blister pack to be aerosolized in the surrounding air and may create a synthetic jet that distributes the medicament into the flow channel 30. The medicament is then transported into the patient's inhalation air stream drawn through the mouthpiece 2.

The vibrating element may be activated by flow sensor 60 which senses the breath of the patient as described in U.S. Pat. No. 6,152,130 and in co-pending U.S. application Ser. No. 11/064, 201, both of which are commonly owned and are incorporated herein by reference. Referring to FIGS. 10-12, flow element 60 is comprised of flow sensor 61, the signal of which is conditioned 201 and send to a microprocessor 203. The control logic within the microprocessor, in connection with the system clock circuit 202, controls the vibrating element such as piezoelectric transducer 41 through driver circuit 206. Power to the vibrating element is supplied by battery 81 which is adjusted by circuit 205. The microprocessor also sends a signal to LEDs 71 of user interface 70 when inhalation is complete. As mentioned above, the microprocessor may also send a signal to user interface 70 when a prescribed time has passed since the previous dose.

Once a blister pack has been emptied, it may be disposed of by extracting the empty blister through the top of the housing next to the mouthpiece 2. Alternatively, it may be stored in the cartridge or otherwise out of the way until all the blister packs are depleted, at which time a fresh cassette may be loaded into the inhaler after the emptied cassette is removed.

FIG. 13 shows the elements of the present invention in an exploded view. The housing 1 may be comprised of multiple pieces, including device cover 4 and chassis 5. the printed circuit board assembly 82, which includes the microprocessor and various circuits, is connected to the flow sensor by flex wire 62. The assembly shown in FIG. 13 may be modified without departing from the principles of the present disclosure. For example, the cam disk may be reduced in size and take a form other than that of a flat disk, and still provide the same function.

Figure 14:
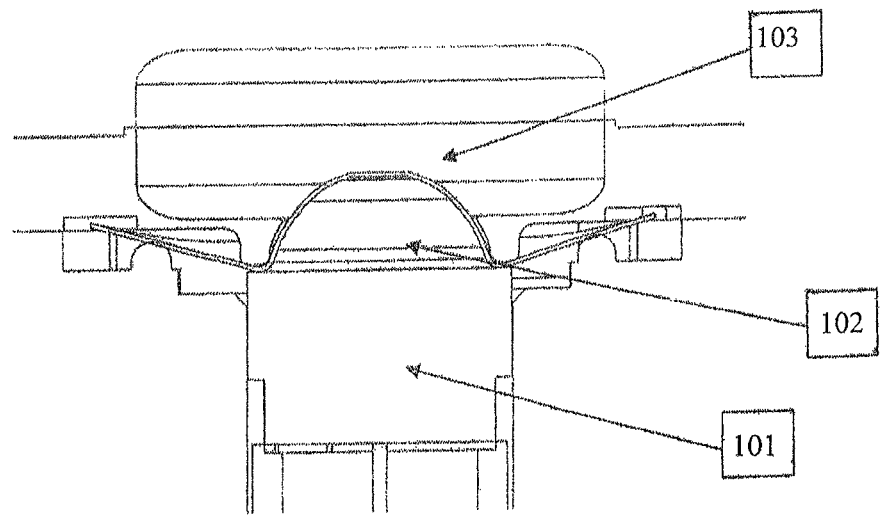

Another aspect of the present disclosure provides an improved device for positioning and clamping a blister in connection with a vibrating element. FIG. 14 illustrates one approach to clamping a powder-containing blister in order to expel the dry powder from the blister using vibratory energy and synthetic jetting, and comprises a vibrator 101, e.g. piezoelectric element, a first chamber 102 and a second chamber 103. Circumferential contact is established between the blister comprising the first chamber and the second chamber on the flange of the first chamber or blister which facilitates contact between the first chamber or blister and the vibratory element. This clamping practice provides for establishment of synthetic jets and delivery of the dry powder from the first chamber or blister 1.

Figure 15:
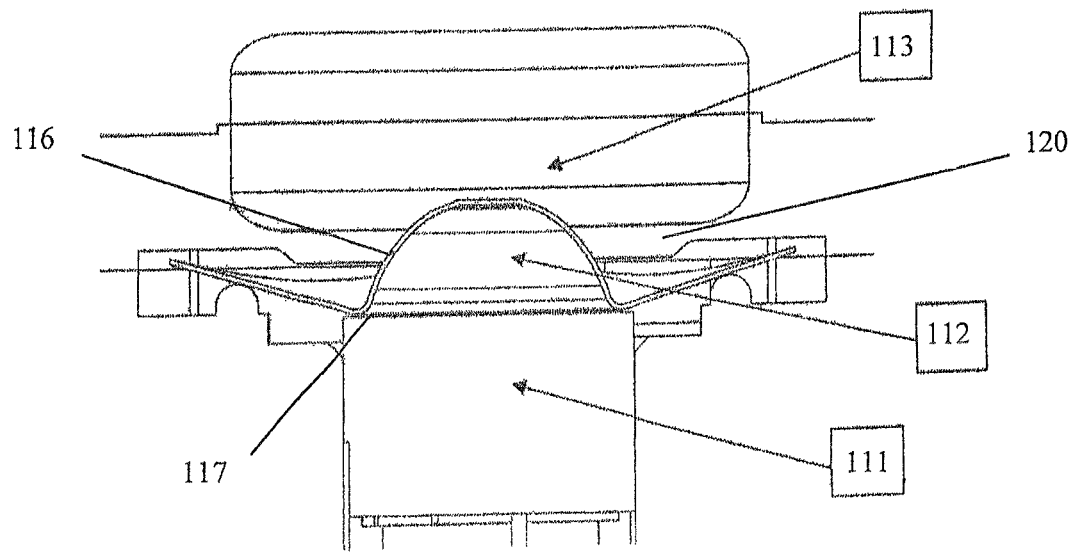

An alternative and preferred clamping mechanism, which significantly improves the powder deagglomeration and consistency of delivery of dry powder inhalers utilizing vibratory elements, is shown in FIG. 15. Referring to FIG. 15, the improved clamping approach provides circumferential contact of the first chamber or blister 112 and the second 113 chamber on the upper wall of the first chamber or blister and facilitates contact between the first chamber or blister and the vibratory element 111. This improved clamping approach is analogous to a ball joint allowing rotational motion between the first chamber or blister and the second chamber and consequently allows co-planarity between the first chamber or blister and the vibratory element. For example, the blister pack may be viewed as comprising two faces; a first face 116 having a crown and a second face 117 being preferably flat in relation to the first face. The flow channel (i.e., the second chamber) of the inhaler includes a blister pack clamping element 120 which allows the top of the crown of the first chamber or blister to be engaged with the flow channel, while maximizing the contact between the second face of the blister and the vibratory element. When positioned within the blister pack clamping element, the clamping element affords the blister pack three rotational degrees of freedom, thereby further ensuring that the blister pack and the vibrating element are properly engaged. As depicted in FIG. 15, the blister pack clamping element preferably will engage the first face of the blister at a location nearer to the top of the crown than to the base of the crown.

Also, with this arrangement, by making contact with the upper wall of the first chamber, vibratory energy for the formation of the synthetic jet is preserved, thereby eliminating any damping that may otherwise result.

To test this feature, identical dry powder inhalers were produced which differed only in the mechanism for clamping the first chamber by the second chamber, e.g. bottom vs. top clamping and were evaluated with the same dry powder and operating conditions; the results demonstrated significant improvement of the top clamp over the bottom clamp in the following measures of performance:

1) Improved consistency of engagement of the first chamber to the piezoelectric element.
2) Lower damping as measured by higher average piezoelectric frequency and lower impedance.
3) Higher peak entrained airspeed of the synthetic jet,
4) Lower first chamber movement, likely preventing shifts in mode of vibration.
5) Higher average aerosol performance and lower variability.

It should be emphasized that the above-described embodiments of the present device and process, particularly, and "preferred" embodiments, are merely possible examples of implementations and merely set forth for a clear understanding of the principles of the disclosure. Many different embodiments of the method and device for clamping a blister within a dry powder inhaler described herein may be designed and/or fabricated without departing from the spirit and scope of the disclosure. For example, the effective delivery of the medicament may be optimized by manipulating the waveform of the piezoelectric vibrator. All these and other such modifications and variations are intended to be included herein within the scope of this disclosure and protected by the following claims. Therefore the scope of the disclosure is not intended to be limited except as indicated in the appended claims.

The invention claimed is:

1. A medication inhaler, comprising
   a housing for accommodating a cartridge including a rotary carousel containing a plurality of individual separate blister packs fanned out in a radial pattern relative to a plane of the rotary carousel, wherein said individual blister packs each contain a medication;
   a vibrating element within the housing;
   a blister pack carrier for moving one blister pack at a time along a radial path into an operating position adjacent a chamber;
   said chamber defining a flow channel communicating with a blister pack, wherein the chamber includes a blister clamping surface to which an individual, separate blister pack may be clamped in position adjacent the vibrating element, said blister clamping surface comprising an opening through which the blister pack engages at least in part with the chamber; and
   a spring for urging the vibrating element against the individual blister pack.

2. The inhaler of claim 1, wherein the blister pack comprises a first face and a second face, the second face being positioned in contact with the vibrating element.

3. The inhaler of claim 1, wherein the vibrating element is a piezoelectric transducer.

4. The inhaler of claim 1, wherein the medication comprises a dry powder.

5. The inhaler of claim 1, wherein the medication comprises a liquid.

6. The inhaler of claim 1, further comprising a flow sensor for sensing the breath of the user, and an electrical circuit for activating the vibrating element.

7. The inhaler of claim 1, further comprising a battery and a printed circuit board.

8. The inhaler of claim 1, wherein the blister pack comprises a first face and a second face, the first face having a crown, the first face being engaged at least in part with the chamber.

9. The inhaler of claim 8, wherein the blister clamping surface allows three rotational degrees of freedom between the chamber and the blister pack.

10. The inhaler of claim 8, wherein the blister clamping surface surrounds, at least in part, the crown of the blister pack.

11. The inhaler of claim 10, wherein the blister clamping surface engages the first face of the blister pack that is closer to the top of the crown than to the base of the crown.

* * * * *

UNITED STATES PATENT AND TRADEMARK OFFICE
CERTIFICATE OF CORRECTION

| | | |
|---|---|---|
| PATENT NO. | : 8,985,101 B2 | Page 1 of 1 |
| APPLICATION NO. | : 13/840577 | |
| DATED | : March 24, 2015 | |
| INVENTOR(S) | : Kent D. Mosier | |

It is certified that error appears in the above-identified patent and that said Letters Patent is hereby corrected as shown below:

On the Title Page

Page 3, References Cited, OTHER PUBLICATIONS, add omitted reference:

International Search Report and Written Opinion issued in related application no. PCT/US14/20371, dated June 5, 2014 (12 pgs).

Signed and Sealed this
Twenty-second Day of September, 2015

Michelle K. Lee
*Director of the United States Patent and Trademark Office*